(12) United States Patent
Chiang

(10) Patent No.: US 6,405,731 B1
(45) Date of Patent: Jun. 18, 2002

(54) VENTILATIVE JOINT GUARD

(76) Inventor: Pang-Ching Chiang, 6F, No. 293, Sec. 4, Chung-Hsiao E. Rd., Taipei (TW)

(*) Notice: Subject to any disclaimer, the term of this patent is extended or adjusted under 35 U.S.C. 154(b) by 0 days.

(21) Appl. No.: 09/870,542

(22) Filed: May 30, 2001

(51) Int. Cl.7 .................................................. A61F 5/37
(52) U.S. Cl. ......................... 128/878; 128/879; 602/20
(58) Field of Search .................................. 128/869, 877, 128/878, 879, 846; 602/20, 23, 26, 60, 61

(56) References Cited

U.S. PATENT DOCUMENTS 4,832,010 A * 5/1989 Lerman .............................. 2/2
5,085,210 A * 2/1992 Smile ............................ 602/26
5,865,776 A * 2/1999 Springs ........................ 602/26

* cited by examiner

*Primary Examiner*—Michael A. Brown
(74) *Attorney, Agent, or Firm*—Dellett and Walters

(57) ABSTRACT

A ventilative joint guard is composed of a neoprene outer portion (10) and an elastic fiber textile inner portion (20). The joint guard provides a physical heating treatment, however, variation in the texture of the elastic fiber textile of the inner portion (20) makes the joint guard have excellent ventilation and makes users still feel comfortable after having worn the joint guard for a period of time.

4 Claims, 6 Drawing Sheets

VENTILATIVE JOINT GUARD

BACKGROUND OF THE INVENTION

1. Field of the Invention

The present invention relates to a joint guard, and more particularly a ventilative joint guard that provides physical treatment and comfort to users.

2. Description of Related Art

With the improvement of life quality, people have become especially interested in active sports in their leisure time to improve their health and feel fulfilled. However, joints injuries are usually caused when people do not have proper warm-up or exercise excessively. Such injuries may be serious and permanent such that the sports about which people feel passionate can no longer be pursued. Therefore, many sport fans or athletes wear joint guards to protect their joints when they are doing some exercises. Additionally, people who have already gotten hurt at joints have more requirements than others less affected and so must wear guards to avoid second injuries. However, conventional sport guards still have some disadvantages and need to be improved.

For example, a conventional guard is shown in FIG. 5, wherein the guard (50) is composed of a first part (51) and a second part (53). The first part (51) has larger area than the second part (53), and these two parts are both made of neoprene and sewed with each other to form a sleeve. When the guard (50) is sleeved on the joint of a limb, take an arm for example, the second part (53) is an inward face to place on the joint and is sandwiched between an upper portion and a lower portion of the arm. Although neoprene is elastic, the guard (50) made of neoprene has a certain thickness and hence, when the arm is bent (see FIG. 6), several wrinkles (52) are formed at the joint and cause an uncomfortable feeling and hindrance in movement.

Beside, the neoprene is a compactly vesicant material and does not disperse heat easily so that it provides a physical heat treatment. However, the neoprene lacks sufficient ventilation quality and excessive heat accumulated inside the guard (50) makes users feel uncomfortable. Even worse is that the heat, moisture and sweat mix together to create a breeding ground for germs, and this results irritation of skin after the guard has been worn for a period of time.

To overcome the shortcomings, the present invention tends to provide a ventilative joint guard to mitigate and obviate the aforementioned problems.

SUMMARY OF THE INVENTION

The main objective of the invention is to provide a ventilative joint guard that does not experience uncomfortable wrinkles at a joint of limb.

Another objective of the invention is to provide a ventilative joint guard that provides a heat treatment and make users still feel comfortable after having worn the guard for a period of time.

Other objects, advantages and novel features of the invention will become more apparent from the following detailed description when taken in conjunction with the accompanying drawings.

DETAILED DESCRIPTION OF PREFERRED EMBODIMENT

Figure 1:
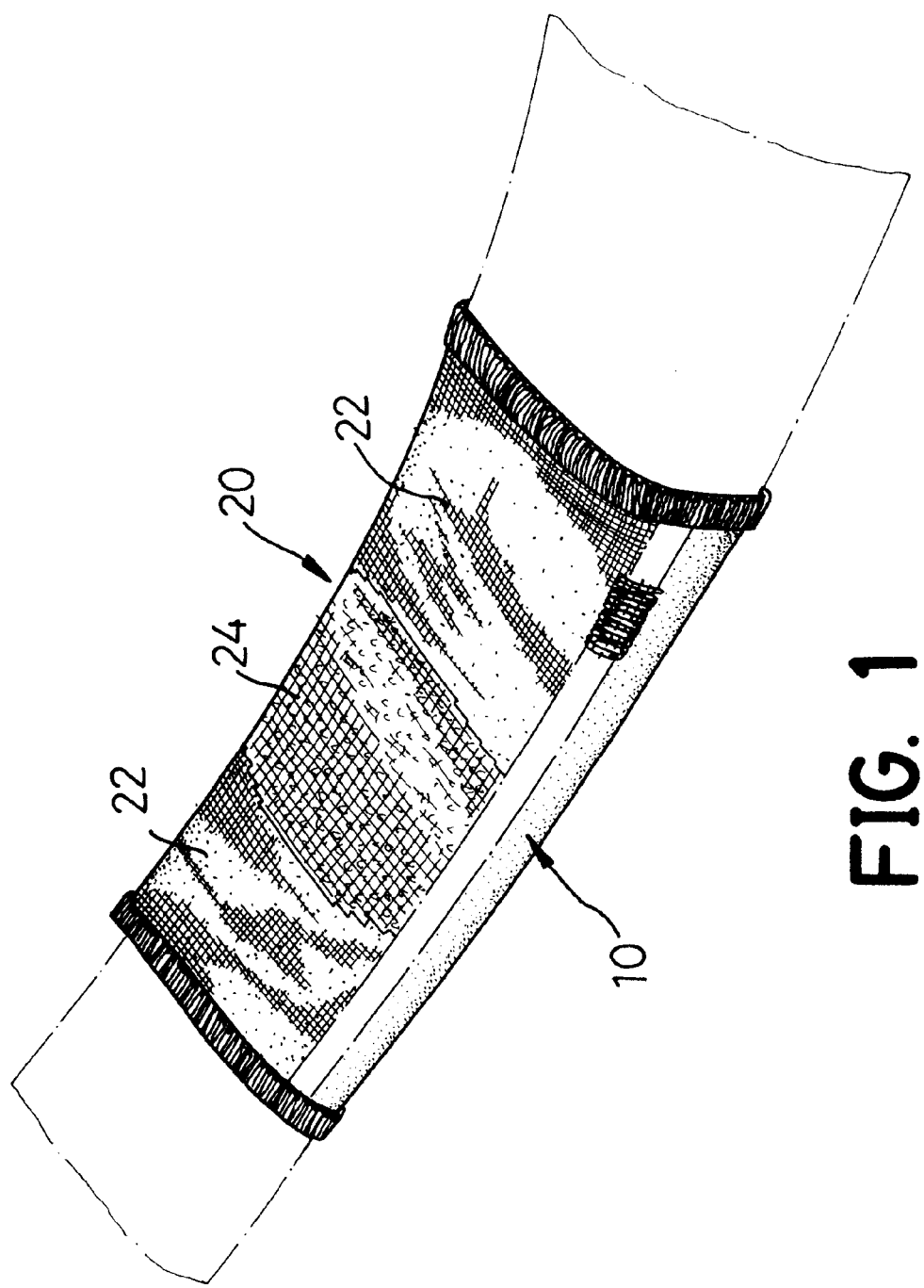
FIG. 1 is a perspective view of a ventilative joint guard in accordance with the present invention.

With reference to FIG. 1, a ventilative joint guard is composed of an outer portion (10) and an inner portion (20). The outer portion (10) and the inner portion (20) are sewn together to form a tube to sleeve a joint of a limb.

The outer portion (10) is made of neoprene, and is placed at the outside position of the joint. The outer portion (10) takes up a larger area proportion of the joint guard than the inner portion (20).

The inner portion (20) is made of elastic fiber textile the same material as an elastic medical bandage, and the inner portion (20) is placed at the inner position of the joint and takes up a small area proportion of the joint guard than the outer portion (10).

In this invention, the inner portion (20) is divided into two compact areas (22) and a slack area (24) distinguished by different weaves. In FIG. 1, the slack area (24) is constructed between the two compact areas (22).

Figure 4:
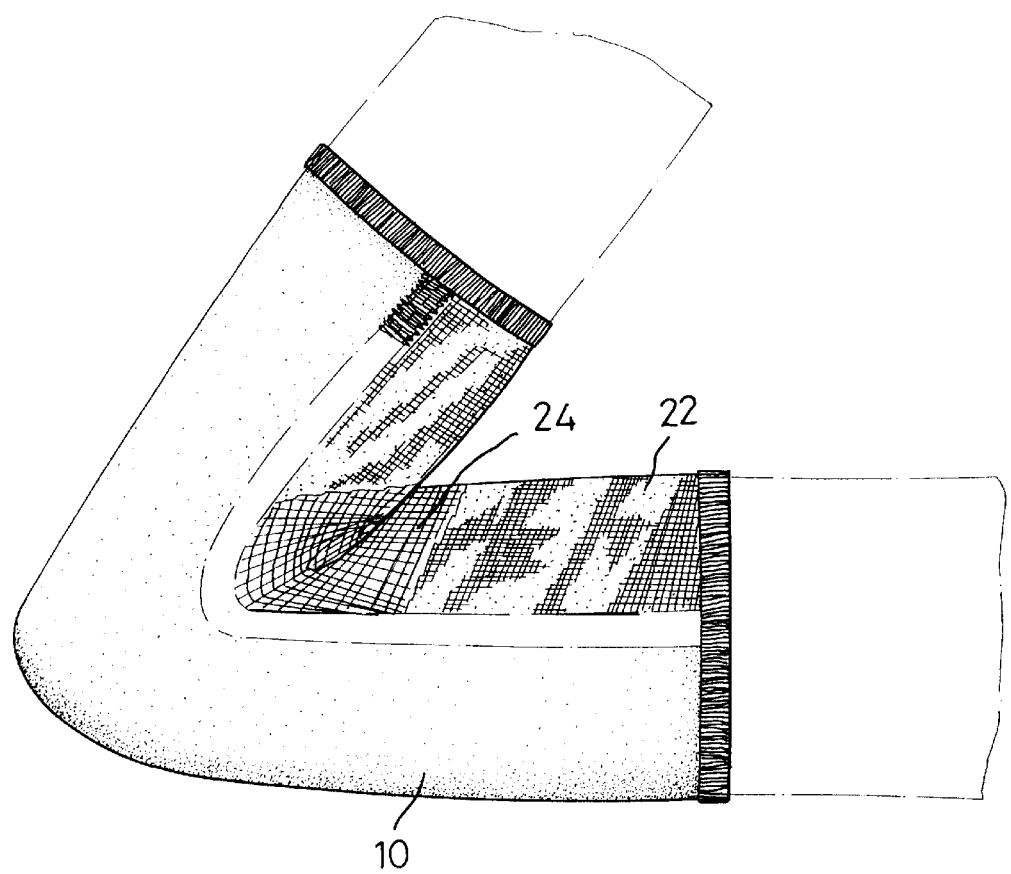
FIG. 4 is a perspective view of the ventilative joint guard in accordance with FIG. 1, when the ventilative joint guard is worn on a bent arm.
Figure 5:
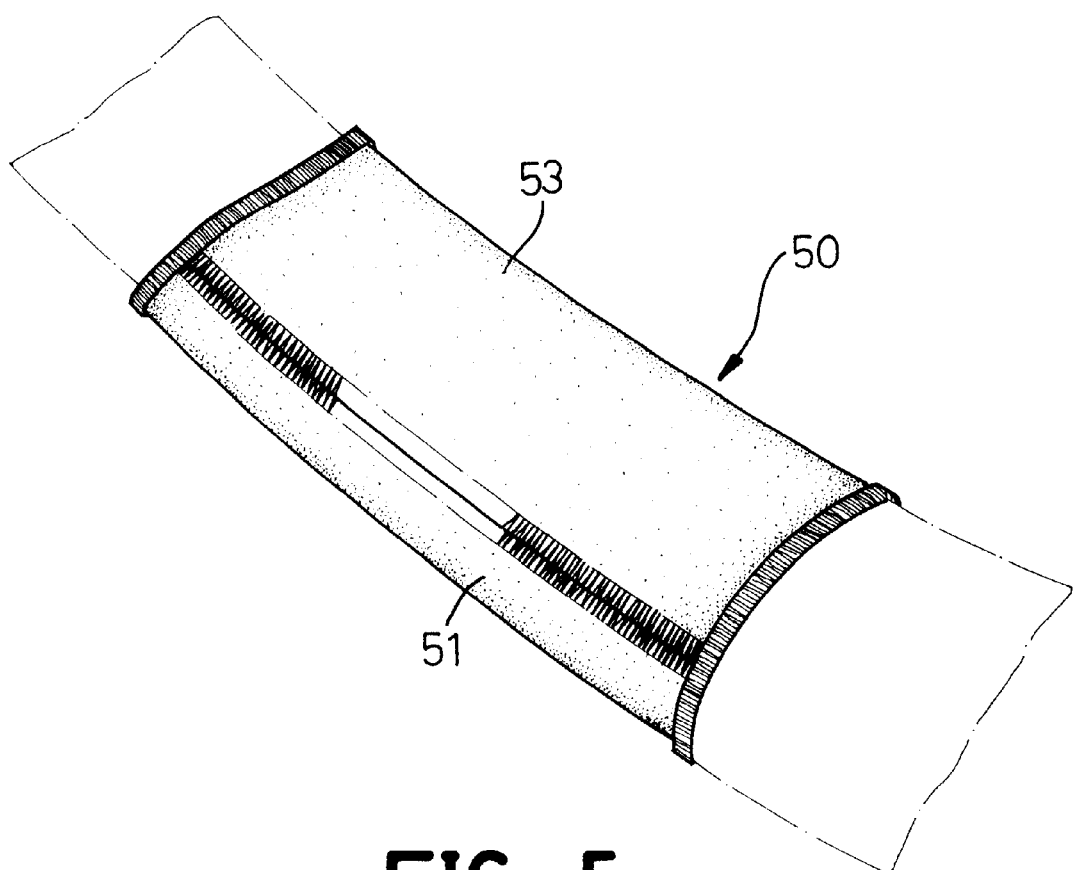
FIG. 5 is a perspective view of a conventional guard.
Figure 6:
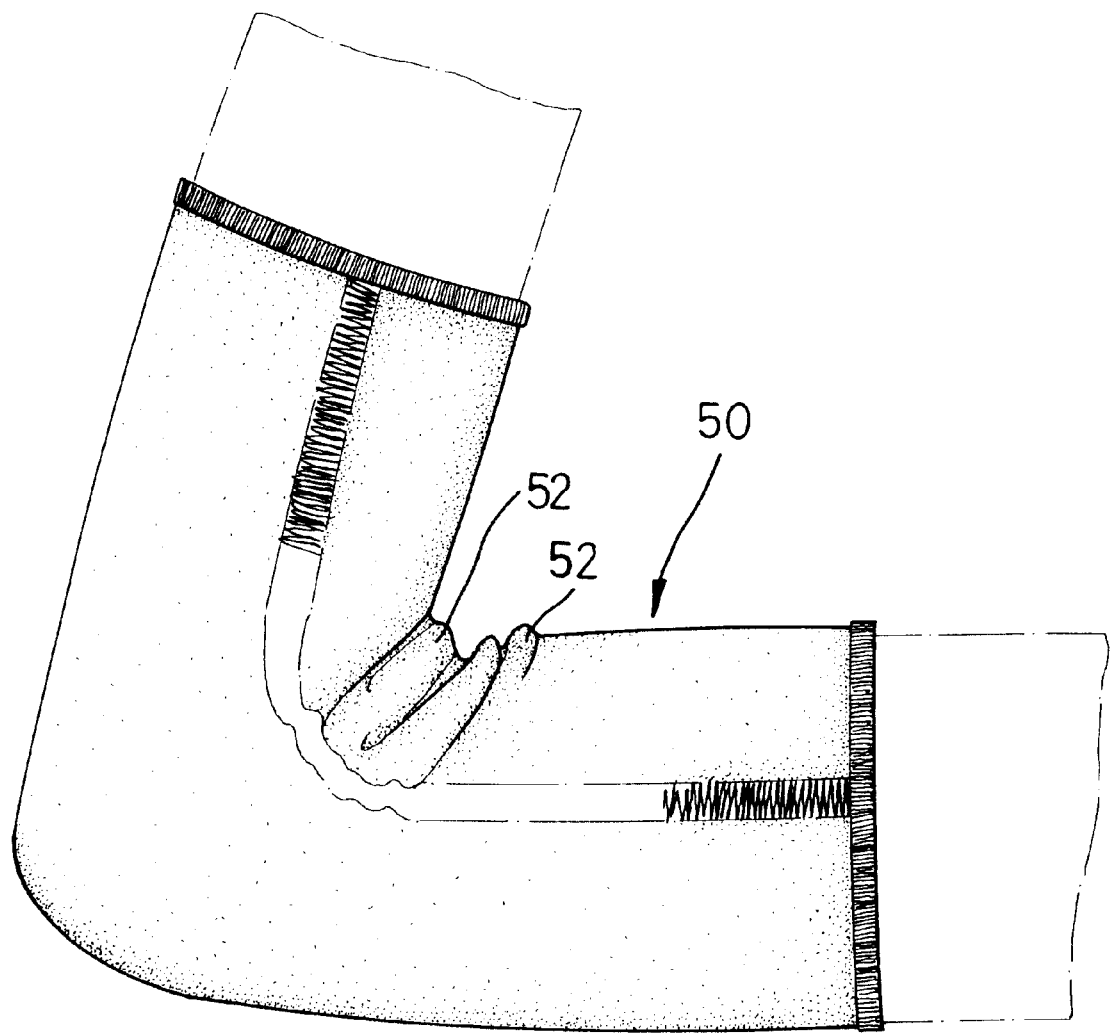
FIG. 6 is a perspective view of the conventional guard in accordance with FIG. 5 when the conventional guard is worn on a bent arm.

The arrangement of the ventilative joint guard makes the joint mainly protected by outer portion (10) and retains natural heat of the joint to achieve a heat treatment. Furthermore, the outer portion (10) also securely fixes the joint guard on the limb by its elasticity. The elastic fiber textile of the inner portion (20) is softer and thinner than the neoprene texture so that when the inner portion (20) is placed on the bent joint, the elastic fiber textile has few wrinkles (see FIG. 4). Therefore, users feel comfortable and are not restricted when they move their limbs when wearing this ventilative joint guard.

Additionally, the elastic fiber textile of the inner portion (20) has large mesh so that it has excellent ventilation. Particularly, the different weave textures of the compact area (22) and the slack area (24) satisfy different requirements in ventilation of the joint guard.

Figure 2:
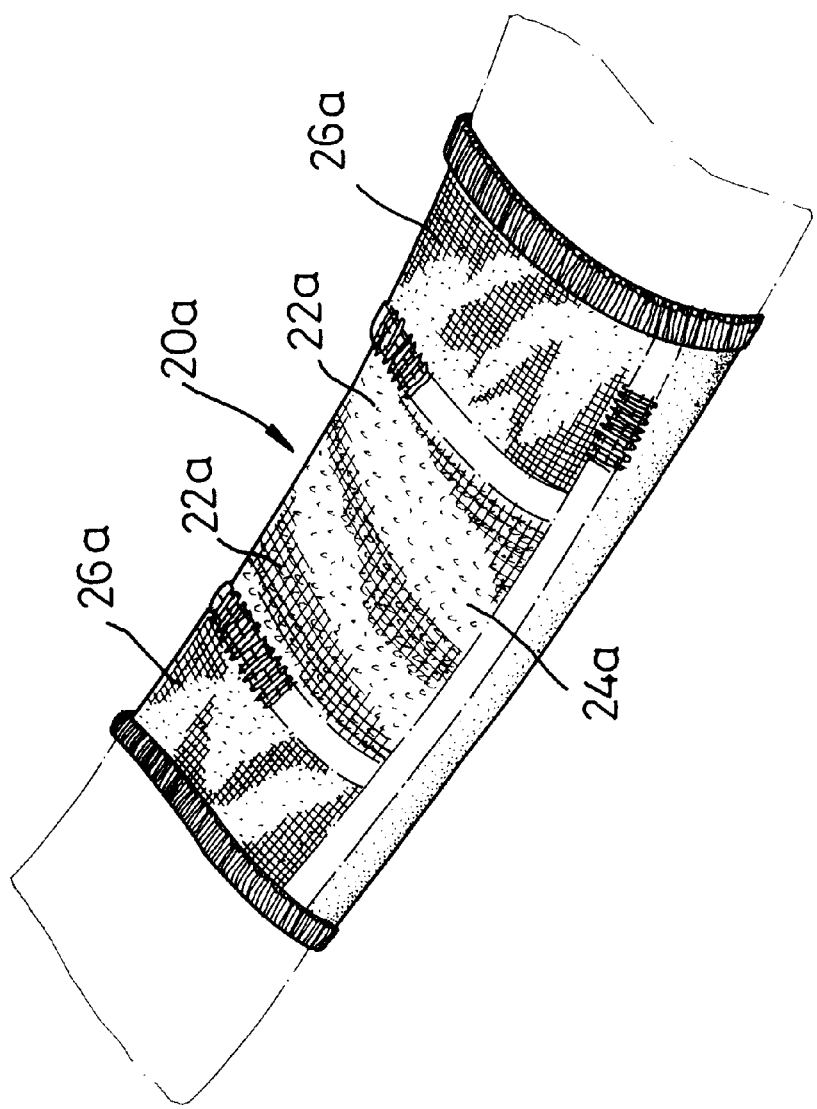
FIG. 2 is a perspective view of a first preferred embodiment of the ventilative joint guard.

Now with reference to FIG. 2, in a first preferred embodiment of the ventilative joint guard, the inner portion (20a) has two compact areas (22a) sandwiching the slack area (24a) and two additional strengthening areas (26a). Each strengthening area (26a) is made of neoprene and formed at two sides of the inner portion (20a) respectively to enhance the positioning force of the joint guard.

Figure 3:
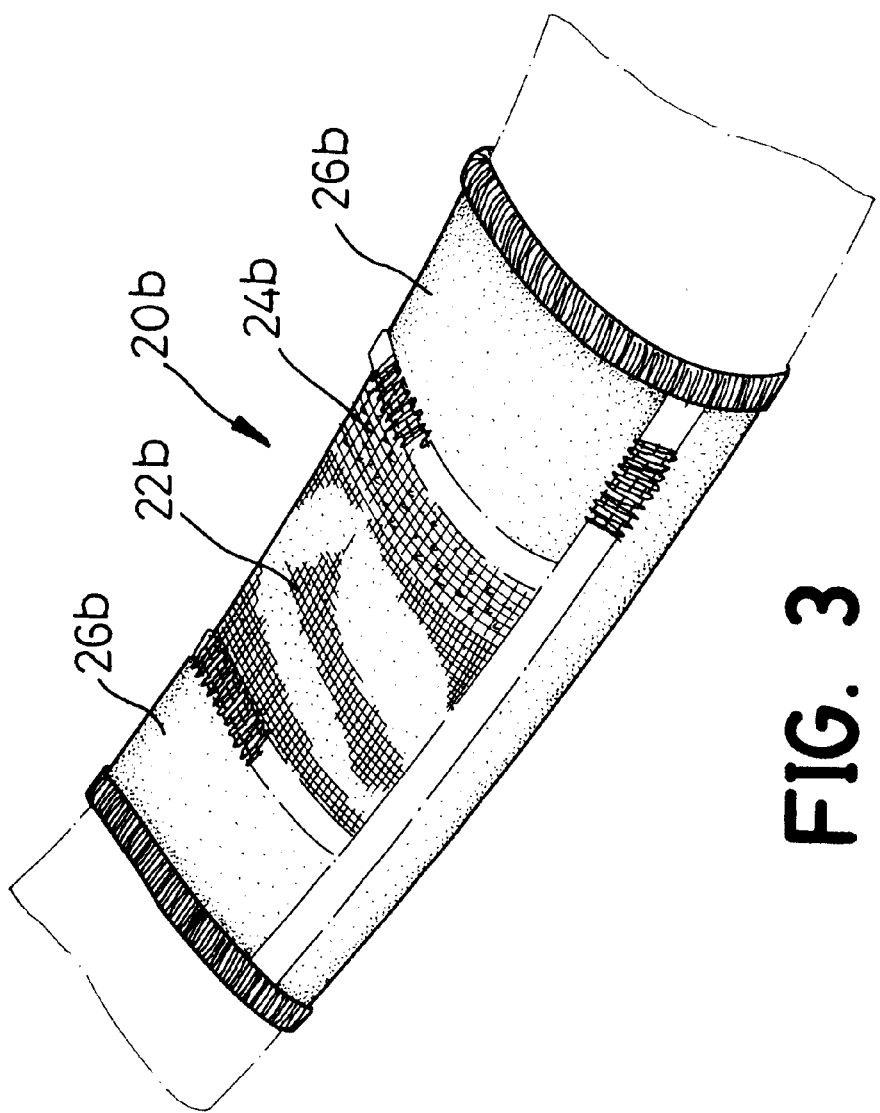
FIG. 3 is a perspective view of a second preferred embodiment of the ventilative joint guard.

FIG. 3 shows a second preferred embodiment of the ventilative joint guard, the inner portion (20b) has one compact area (22b), one slack area (24b) and two additional strengthening areas (26b). The two strengthening areas (26b) are formed at two sides of the inner portion (20b) the same as shown in FIG. 2 and the slack area (24b) is formed at one side of the compact area (22b), not in the middle of the compact areas (22b).

The second preferred embodiment is designed according to different injured parts for users. For example, the injured parts are at upper portions and lower portions around the joints, wherein users need to position the joint guards high or low to protect the injured parts of the limbs.

Therefore, it is to be understood, that even characteristics and advantages of the present invention have been set forth in the foregoing description together with details of the structure and function of the invention. The disclosure is illustrative only, and changes may be made in detail, especially in arrangement of parts of the inner portion (20) within the principles of the invention to the full extent indicated by the broad general meaning of the terms in which the appended claims are expressed.

What is claimed is:

1. A ventilative joint guard for a joint of a limb, the joint guard comprising:

an outer portion (10) adapted to be placed at an outside position of the joint; and an inner portion (20) integrally formed with the outer portion (10) and adapted to be placed at an inner position of the joint, wherein the inner portion (20) is divided into at least one compact area (22) and at least one slack area (24) in different weave textures;

wherein the outer portion (10) is made of neoprene and the inner portion (20) is made of elastic fiber textile.

2. The ventilative joint guard as claimed in claim 1, wherein the inner portion (20) has two strengthening areas (26) formed at two edge sides of the inner portion (20) to enhance a positioning force of the joint guard with respect to the limb.

3. The ventilative joint guard as claimed in claim 1, wherein the slack area (24) is sandwiched between two of the compact areas (22).

4. The ventilative joint guard as claimed in claim 2, wherein the slack area (24) is sandwiched between two of the compact areas (22).

* * * * *